(12) United States Patent
Suga et al.

(10) Patent No.: US 9,280,642 B2
(45) Date of Patent: Mar. 8, 2016

(54) METHOD OF MANAGING CLINICAL TESTING APPARATUS, CLINICAL TESTING SYSTEM, AND MAINTENANCE MANAGEMENT APPARATUS

(75) Inventors: Yusuke Suga, Kobe (JP); Naoki Shindo, Palatine, IL (US); Atsumasa Sone, Akashi (JP); Hiroyuki Koyama, Kobe (JP); Shunsuke Ariyoshi, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 960 days.

(21) Appl. No.: 13/459,848

(22) Filed: Apr. 30, 2012

(65) Prior Publication Data

US 2012/0283980 A1 Nov. 8, 2012

(30) Foreign Application Priority Data

May 2, 2011 (JP) .................................. 2011-102819

(51) Int. Cl.
*G01R 35/00* (2006.01)
*G06F 19/00* (2011.01)
*G01N 35/00* (2006.01)

(52) U.S. Cl.
CPC ........ *G06F 19/366* (2013.01); *G01N 35/00623* (2013.01); *G01N 35/00871* (2013.01); *G05B 2219/24001* (2013.01); *G05B 2219/2657* (2013.01)

(58) Field of Classification Search
CPC .............. A61M 5/172; G01N 33/5302; G01N 33/5438; G01N 15/10; G01N 2203/0048; G01N 2203/0242; G01N 2203/027; G01N 2203/0274; G01N 2496/80; G01N 27/403; G01N 27/49; G01N 33/487; G01N 33/48728; G01N 33/96; G01N 3/01
See application file for complete search history.

(56) References Cited

U.S. PATENT DOCUMENTS 4,612,340 A * 9/1986 Ohachi .......................... 524/296
2008/0006081 A1 * 1/2008 Weldon et al. ............... 73/53.01

* cited by examiner

*Primary Examiner* — Elias Desta
(74) *Attorney, Agent, or Firm* — Brinks Gilson & Lione

(57) ABSTRACT

A management system connected with a clinical testing apparatus is disclosed. The system acquires, from the clinical testing apparatus, a parameter that varies according to deterioration of the unit at a plurality of points of time, stores the parameters and/or analysis results that are obtained by analyzing the parameters, and provides a screen data for showing the stored parameters and/or the stored analysis results in a time-series format. A method for managing a clinical testing apparatus and a clinical testing system for the method are also disclosed.

17 Claims, 10 Drawing Sheets

FIG.4

Data table of pressure data (Time required to reach standard pressure)

| Receiving number | Date received | Time received | Model code | Apparatus ID | Time required to reach standard pressure |
|---|---|---|---|---|---|
| 9871245 | 2011/7/18 | 8:52:59 | CR5000 | 470842 | 9000 |
| 9871244 | 2011/7/18 | 8:52:34 | XD4000 | 59474 | 8700 |
| 9871243 | 2011/7/18 | 8:50:49 | YR2100 | 493290 | 11100 |
|  |  |  |  |  |  |
|  |  |  |  |  |  |

(a) Apparatus ID: 470842 analysis data table of pressure data (time required to reach standard pressure)

| Item | 7/1 | 7/2 | 7/3 | 7/4 | 7/5 | 7/6 | 7/7 | 7/8 | 7/9 | 7/10 | 7/11 | 7/12 | 7/13 | 7/14 | 7/15 | 7/16 | 7/17 | 7/18 |
|---|---|---|---|---|---|---|---|---|---|---|---|---|---|---|---|---|---|---|
| 1st | 8100 | 800 | 8400 | | 8700 | 8600 | 9000 | 8600 | 8600 | 800 | | 8700 | 9300 | 9900 | 9100 | 8800 | 8900 | 9000 |
| 2nd | | 8400 | | | | | 9400 | | | | | | | | | | | |
| 3rd | | | | | | | 8800 | | | | | | | | | | | |
| Avr. | 8100 | 8400 | 8400 | | 8700 | 8600 | 9067 | 8600 | 8600 | | | 8700 | 9300 | 9900 | 9100 | 8800 | 8900 | 9000 |
| M. Avr. | | | | | | 8480 | 8673 | 8713 | 8753 | | | 8753 | 8853 | 9020 | 9120 | 9160 | 9200 | 9140 |

(b) ⟨Daily Average⟩

(c) ⟨Moving Average⟩

FIG.7

Data table of temperature data

| Receiving number | Date received | Time received | Model code | Apparatus ID | Environmental temp | Temp adjust time |
|---|---|---|---|---|---|---|
| 2263078 | 2011/7/17 | 9:07:03 | XX1000 | 567891 | 27.8 | 362 |
| 2263077 | 2011/7/17 | 9:06:35 | XC2000 | 234567 | 27.3 | 289 |
| 2263076 | 2011/7/17 | 9:02:12 | XD4000 | 890123 | 23.4 | 389 |
|  |  |  |  |  |  |  |
|  |  |  |  |  |  |  |

METHOD OF MANAGING CLINICAL TESTING APPARATUS, CLINICAL TESTING SYSTEM, AND MAINTENANCE MANAGEMENT APPARATUS

RELATED APPLICATIONS

This application claims priority under 35 U.S.C. §119 to Japanese Patent Application No. 2011-102819 filed on May 2, 2011, the entire content of which is hereby incorporated by reference.

BACKGROUND OF THE INVENTION

1. Field of the Invention

The present invention relates to a method of managing clinical testing apparatus, clinical testing system, and maintenance management apparatus.

2. Description of the Related Art

When a clinical testing apparatus such as a blood analyzer malfunctions, accurate analysis results would not be obtained. This may cause an interruption of operations in the testing facility. In this regard, several attempts to make it possible that a maintenance of a clinical testing apparatus, such as exchange of parts, maintenance, or inspection of equipment should be done before a failure occurs in the clinical testing apparatus have been proposed.

U.S. Pat. No. 7,047,142 discloses a monitoring system for detecting foretaste of abnormality in a clinical testing apparatus. In this monitoring system, a condition (predictive condition) that detecting a foretaste of abnormality is pre-stored by a host computer, and the host computer periodically acquires status data from the clinical testing apparatus. The status data include a radiation intensity of lamp, a number of uses of a syringe pump and the like. The host computer compares the pre-stored predictive condition with the received status data, and outputs a high possibility of abnormality occurring when the status data match the predictive condition.

It is useful to know about deterioration of a unit over time so that suitable maintenance and inspection can be performed on the clinical testing apparatus. For example, when a unit gradually deteriorates due to long-term use, there is a possibility of part of the unit can be repaired to eliminate the deterioration. On the other hand, since there may be suspicion of an abnormality when a unit rapidly deteriorates within a short time, there is a possibility that repairing just a part of the unit will be insufficient and that replacement of the unit may be required. The aforementioned art disclosed in U.S. Pat. No. 7,047,142 does not address these problems.

SUMMARY OF THE INVENTION

The first aspect of the present invention is a method for managing a clinical testing apparatus that performs a test on a clinical sample by use of a unit; the method comprising: acquiring, from the clinical testing apparatus, a parameter that varies according to deterioration of the unit at a plurality of points of time; storing the parameters and/or analysis results that are obtained by analyzing the parameters; and displaying the stored parameters and/or the stored analysis results in a time-series format.

The second aspect of the present invention is a clinical testing system comprising: a maintenance computer having a memory and a display; and a clinical testing apparatus connected to the maintenance computer via a network, the clinical testing apparatus having: a unit used for testing a clinical sample; and a transmitting section for transmitting to the maintenance computer a parameter that varies according to deterioration of the unit; wherein the transmitting section transmits the parameter with a predetermined transmission timing; the memory associates and stores the parameters transmitted from the transmitter and/or the analysis result acquired by analyzing the parameters with an identification of the clinical testing apparatus that transmitted the parameters; and the display shows, in response to a display request from a terminal device, the stored parameters or the analysis results of the clinical testing apparatus specified by the identification in time-series format.

The third aspect of the present invention is a management system connected via a network with a clinical testing apparatus that performs a test on a clinical sample by use of a unit, the management system comprising: a receiving section for receiving a parameter transmitted from the clinical testing apparatus at a predetermined timing, the parameter being variable according to deterioration of the unit; a data storage for storing the received parameters and/or analysis results that are obtained by analyzing the received parameters, in association with an identification of the clinical testing apparatus that had transmitted the parameter; and a data provider for providing data of a screen on which the parameters of the unit and/or the analysis results of the clinical testing apparatus identified by one identification is shown in a time-series format.

BRIEF DESCRIPTION OF THE DRAWINGS

FIG. 4 shows a pressure data table;

FIG. 7 shows a temperature control data table;

DETAILED DESCRIPTION OF THE PREFERRED EMBODIMENTS

The embodiments of the clinical testing system of the present invention are described in detail hereinafter with reference to the accompanying drawings.

[1. General Structure]

Figure 1:
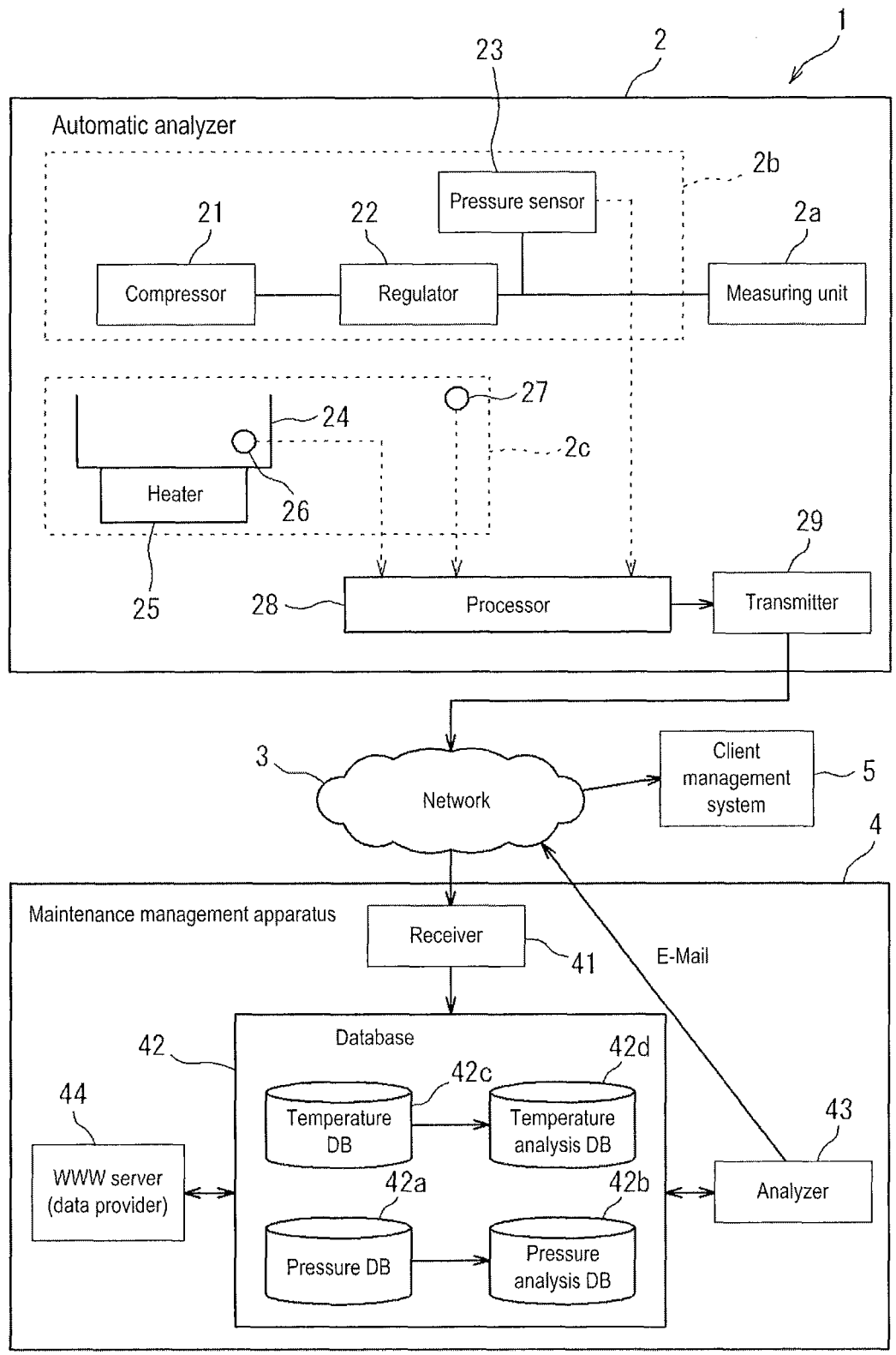
FIG. 1 is a structural view of a clinical testing system.

As shown in FIG. 1, a clinical testing system 1 has a clinical testing apparatus 2, and a maintenance management apparatus 4 connected via a network 3 with the clinical testing apparatus 2.

[2. Clinical Testing Apparatus]

The clinical testing apparatus 2 is a blood analyzer that measures a blood sample collected from a patient as a clinical sample, analyzes the data acquired by the measurement, and generates and outputs the analysis results. More specifically, the clinical testing apparatus 2 is a blood cell counter that counts the blood cell components such as reticulocytes, leukocytes, and platelets that are contained in the blood sample.

The clinical testing apparatus 2 has a plurality of units associated with testing blood samples and which are used to test the blood samples. The units of the clinical testing apparatus 2 include a measuring unit 2a for measuring a blood sample, an air pressure source unit 2b for operating an air pressure device provided in the measuring unit 2a, and a heating unit 2c for heating the reagent to be mixed with the blood sample, as well as various other units.

The measuring unit 2a is provided with a sample preparation part for preparing a measurement sample by mixing reagent and blood sample, an electrical type measuring part for measuring the electrical properties of the measurement sample by applying a voltage to the prepared measurement sample, and an optical type measuring part for measuring the optical properties of the measurement sample by irradiating light on the measurement sample via a laser diode. After the measurement is completed, the measurement sample is stored in a waste chamber. The waste fluid is discharged from the waste chamber to outside the apparatus when a fixed amount of fluid is stored in the waste chamber.

The air pressure source unit 2b is provided with a compressor 21 for discharging compressed air, and a regulator 22 for adjusting the pressure of the air discharged from the compressor 21 to a desired pressure. A pressure sensor 23 is provided in the airflow path on the output side (measuring unit 2a side) of the regulator 22. The air output from the regulator 22 is used as positive pressure or negative pressure to move a liquid of either the blood sample or reagent within the apparatus.

The heating unit 2c is provided with a container 24 for holding reagent, and a heater 25 for heating the reagent contained in the container 24 to a desired temperature by heating the container 24. A first temperature sensor 26 for measuring the temperature of the reagent is provided near the heater 25. A second temperature sensor 27 for measuring the environmental temperature (temperature of the atmosphere within the clinical testing apparatus 2) is provided at a position sufficiently separated from the heater 25 within the clinical testing apparatus 2.

The pressure sensor 23, first temperature sensor 26, and second temperature sensor 27 are respectively connected to a processor 28. The measurement results of the various sensors 23, 26, 27 are forwarded to the processor 28.

The processor 28 acquires the measurement values of the sensors 23, 26, and 27 with a predetermined timing. The processor 28 generates the deterioration parameters (parameters with variable values depending on the deterioration of the unit) of the units 2b and 2c based on the acquired measurement values.

The processor 28 starts the air pressure source unit 2b, then determines the time (time to reach standard pressure) until the output of the regulator 22 reaches a predetermined condition (standard pressure). Note that the predetermined pressure is the pressure required to operate the measuring unit 2a. That is, the output of the regulator 22 must reach the standard pressure in order for the clinical testing apparatus 2 to be capable of measuring blood, the test substance.

When the compressor 21 is started, compressed air is supplied from the compressor 21 to the regulator 22, and the output of the regulator 22 gradually increases until the standard pressure is reached. However, as the compressor 21 deteriorates, a longer time is required after starting in order to reach the standard pressure since the amount of airflow is reduced. This deterioration occurs before complete failure of the compressor 21 occurs and gradually increases over time, hence gradually increasing the time needed to reach the standard pressure.

The time required to reach standard pressure is determined by the processor 28 as the time from when the compressor 21 is started until the output of the pressure sensor 23 reaches the standard pressure. The time required to reach the standard pressure is a deterioration parameter that varies (increases) according to the deterioration of the compressor 21 of the air pressure source unit 2b. Note that starting of the compressor 21 is accomplished as follows. A power button (not shown in the drawing) is provided for the clinical testing apparatus 2, and the power source of the clinical testing apparatus 2 is turned ON when the power button is pressed by the user. When the power source is turned ON, the compressor 21 is started in conjunction therewith, and the compressed air discharge starts. Accordingly, the time at which the compressor 21 is started is the time at which the power source of the clinical testing apparatus 2 is turned ON.

The transmitting section 29 transmits via the network the each measurement of the time required to reach standard pressure acquired by the processor 28 to the maintenance management apparatus 4.

When the transmitting section 29 transmits the deterioration data of the time required to reach the standard pressure, the associated identification of the clinical testing apparatus 2 (apparatus ID) and/or the device code are also transmitted.

The processor 28 starts (energizes) the heating unit 2c, then determines the time (heat adjustment time) until the reagent to be heated reaches a predetermined temperature (for example, 41° C.) as the deterioration parameter of the heating unit 2c. The reagent must be heated approximately to body temperature to react the reagent and the blood to be tested at the same temperature as the body. That is, the reagent must reach the predetermined temperature so that the clinical testing apparatus 2 can measure the blood that is the object of the test.

Although the heater 25 raises the temperature when current starts, heating efficiency decreases as the performance of the heater 25 deteriorates, thus making it difficult to raise the temperature and increasing the time until the predetermined temperature is reached. This deterioration occurs before complete failure of the heater 25 occurs and gradually increases over time, hence increasing the time until the predetermined temperature is reached.

The time until the predetermined temperature is reached is the time from when the processor 28 starts the heater 25 until output indicates the predetermined temperature, and this time is the temperature adjustment time.

Since the temperature adjustment time is dependent on the fluctuation of the environmental temperature (atmospheric temperature within the clinical testing apparatus 2), the environmental temperature is required to accurately comprehend the deterioration condition.

The processor 28 acquires the environmental temperature from the second temperature sensor 27 when the temperature adjustment time is measured. The temperature adjustment time and the environmental temperature are deterioration parameters that vary (increase) according to the deterioration of the heater 25 of the heating unit 2c.

The processor 28 measures the temperature adjustment time and the environmental temperature each time the heater 25 is started.

The transmitting section 29 transmits, to the maintenance management apparatus 4 via the network, each measurement of the temperature adjustment time and the environmental temperature acquired by the processor 28.

When the transmitting section 29 transmits the deterioration data composed of the temperature adjustment time and the environmental temperature, the associated identification of the clinical testing apparatus 2 (apparatus ID) and the device code are also transmitted.

[3. Maintenance Management Apparatus]

As shown in FIG. 1, the maintenance management apparatus 4 is provided with a receiving section 41 for receiving information forwarded from the clinical testing apparatus 2, database (data storage) 42 for storing information, analyzing section 43 for analyzing the information (deterioration parameters and the like) stored in the database 42, and a WWW server (data provider) 44 for generating data to display information on a terminal device.

The database 42 has a pressure database 42a, pressure analysis database 42b, temperature adjustment database 42c, and temperature analysis database 42d.

Information (deterioration parameters) forwarded from the plurality of clinical testing apparatuses 2 managed by the management apparatus 4 is gradually added to the storage in the pressure database 42a and temperature adjustment database 42c.

That is, the past information forwarded from the several clinical testing apparatuses 2 is stored in the databases 42a and 42c.

The WWW server 44 extracts data from the database 42 according to the display request from a terminal device, and display screen data are generated from the extracted data and transmitted to the terminal device.

Note that the processing functions of the maintenance management apparatus (hereinafter referred to as "management apparatus") 4 are realized by computer-based execution of computer programs. The computer program is stored in a memory device (memory medium; not shown in the drawings) of a computer that configures the management apparatus 4.

Figure 2:
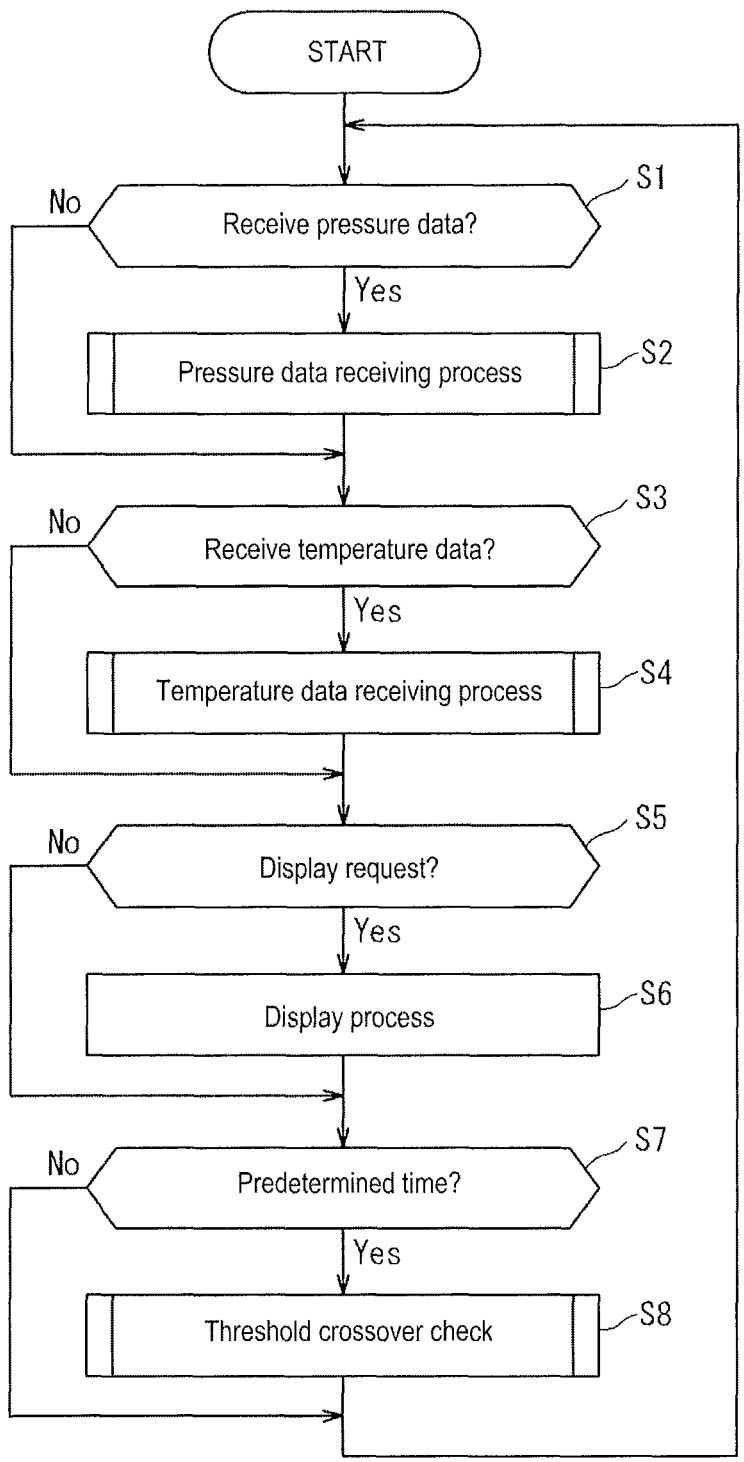
FIG. 2 is a flow chart showing the processing of a maintenance management apparatus.

FIG. 2 shows the sequence of the processes executed by the management apparatus 4.

When the pressure data (time required to reach the standard pressure) deterioration parameter is received (step S1), the management apparatus 4 performs the pressure data receiving process (step S2).

When the temperature adjustment data (temperature adjustment time) and environmental temperature deterioration parameters are received (S2), the management apparatus 4 performs the temperature adjustment data and environmental temperature receiving processes.

When a display request is received from a terminal device (not shown in the drawings) connected to the management apparatus 4 via a network (step S5), the management apparatus 4 performs a process to display the information stored in the database 42 (step S6). The display process is a process to generate and transmit display data in a format (for example, HTML, format) that is displayable on a client (clients of the management system 5) based on the information stored in the database 42.

At a predetermined time (for example 6:00 AM) (step S7), the management apparatus 4 then performs a crossed threshold checking process to confirm whether the information of the database 42 exceeds the threshold (step S8).

Figure 3:
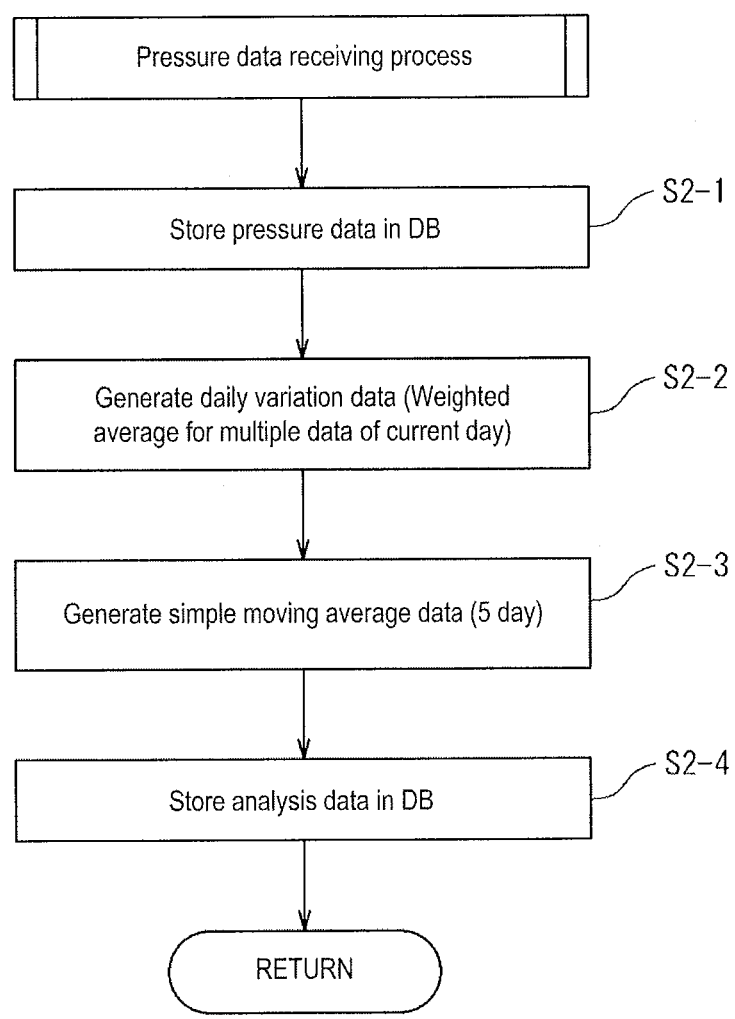
FIG. 3 is a flow chart showing a pressure data receiving process.

In the pressure data receiving process (step S2) shown in FIG. 3, when the receiving section 41 receives the raw data of the pressure data (time required to reach standard pressure) of the deterioration data and the identification of the clinical testing apparatus 2 that sent the data, the raw data are stored in the pressure data database 42a (step S2-1).

FIG. 4 shows the data table structure in the pressure database 42a. The pressure data (time required to reach standard pressure) forwarded from a plurality of clinical testing apparatuses 2 being managed by the management apparatus 4 are stored in the pressure database 42a. Note that the data forwarded from the plurality of clinical testing apparatuses are sequentially added to the storage of the pressure database 42a.

The database structure shown in FIG. 4 includes the reception number, date received, time received, device code, apparatus ID, and time required to reach standard pressure.

The reception number in the database structure is an identifier to distinguish the respective information received by the management apparatus 4. The date and time received are the day and time at which the respective pressure data were received by the management apparatus 4. The stored information can be managed as time-series data by associating and storing the pressure data with the information specifying the date and time received. Note that the date on which the pressure data were acquired by the clinical testing apparatus 2 or the time at which the information was transmitted by the transmitting section 29 of the clinical testing apparatus 2 also may be stored instead of the information specifying the date and time of reception by the management apparatus 4.

The device code and apparatus ID (identification) in the database structure are transmitted together with the pressure data from the clinical testing apparatus 2. By associating and storing the apparatus ID (identification) with the pressure data, the data of a specific clinical testing apparatus 2 can be extracted for analysis or display from among the data of the plurality of clinical testing apparatuses 2 stored in the database 42a.

The time required to reach standard pressure in the database structure is transmitted from the clinical testing apparatus 2.

When the pressure data (time required to reach standard pressure) are stored in the pressure database 42a (step S2-1), the analysis section 43 generates day-to-day variation data as the first analysis data based on the pressure data (time required to reach standard pressure)(step S2-2).

The analysis section 43 generates moving average data as the second analysis data based on the pressure data (time required to reach standard pressure)(step S2-3).

The generated first and second analysis data are stored in the pressure analysis database 42b (step S2-4).

Figure 5:
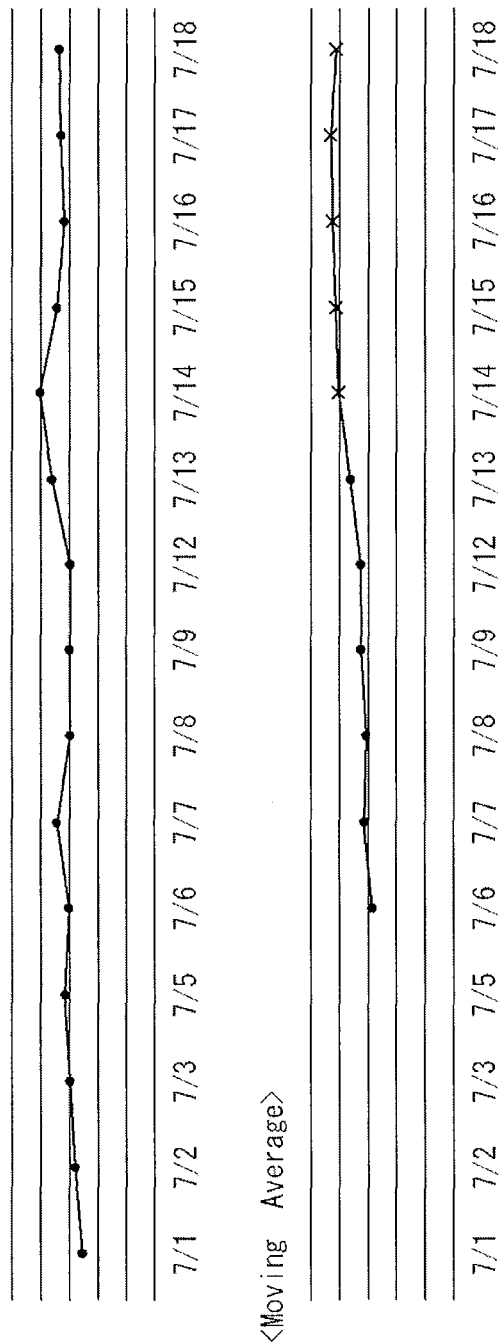
FIG. 5(a) shows a pressure analysis data table, (b) and (c) show examples of analysis data graph.

FIG. 5(a) shows the data table structure of the analysis data (day-to-day variation data and moving average data) related to the time required to reach standard pressure by a specific clinical testing apparatus (apparatus ID: 470842). Note that the analysis data are generated for each of the plurality of clinical testing apparatuses by the analysis section 43. That is, the analysis data of each clinical testing apparatus 2 are stored in the pressure analysis database 42b.

In the data table structure of FIG. 5(a), the item on the horizontal axis is the day (day received). "1st", "2nd", "3rd" amount the items on the vertical axis are where the respective pressure data received on the first, second, and third times for a given day. "Avr." appearing on the vertical axis is where the average value (intra day average) of one or a plurality of pressure data of a given day are stored and become the day-to-day variation data. "M. Avr." appearing on the vertical axis is where the moving average data (simple moving average data) for the past 5 days is stored.

Figure 8:
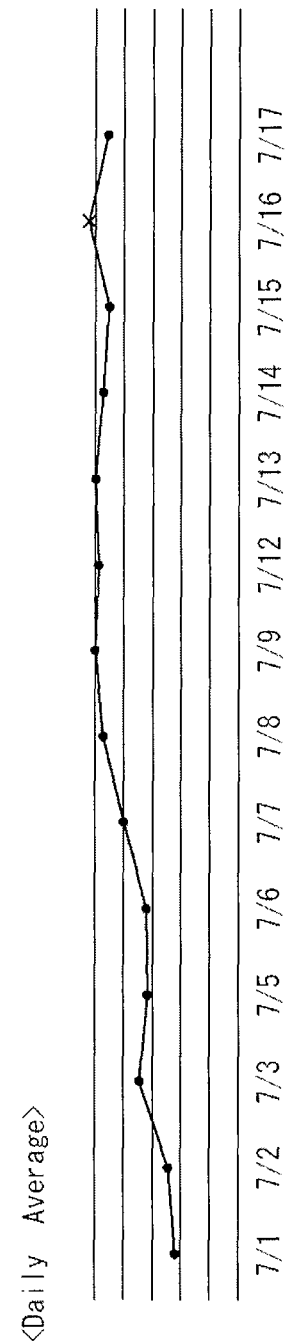
FIG. 8(a) shows a temperature control analysis data table, and (b) shows an example of analysis data table.

Note that the empty fields without data in FIG. 5(a) indicate that no data were received by the management apparatus 4, and the diagonal lines indicate abnormal values that were not used in calculating the average and moving average (similar in FIG. 8(a)).

The raw data of pressure data (time required to reach standard pressure) received by the receiving section is recorded in the pressure database 42a (step S2-1) or either the "1st", "2nd", or "3rd" fields of the pressure analysis database of the clinical testing apparatus specified by the identification (apparatus ID) associated with the raw data in the pressure analysis database 42b.

Note that the initial raw data of the day are recorded in the "1st" field, the second data are recorded in the "2nd" field, and the third data are recorded in the "3rd" field.

The analysis section 43 calculates the average value of the day (weighted average) based on one or a plurality of pressure data of the day as the day-today variation data generating process (step S2-2).

The analysis section 43 generates moving average data from the averages of the five previous days including the current day as the moving average data generating process (step S2-3).

The average value generated in step S2-2 is recorded in the "Avr." field of the pressure analysis database 42b of the clinical testing apparatus specified by the identification (apparatus ID). The moving average value generated in step S2-3 is recorded in the "M. Avr." field of the pressure analysis database 42b of the clinical testing apparatus specified by the identification (apparatus ID).

Note that in FIG. 5(b) the empty fields indicate no data were received. The diagonal lines indicate abnormal data, which were not used to generate the day-today variable data and moving average data (similar to FIG. 8(a)). The abnormal data are below a previously set lower limit threshold. The clinical testing apparatus may be started several times a day, but when restarted, the time from shutdown to the next start up is short. In this case, the next start up is performed before the pressure of the compressor 21 falls so that an unusually short time required to reach standard pressure may be acquired. The management apparatus 4 performs statistical processing to automatically exclude abnormal data from the object of the statistical process so as to not use abnormal data in the statistics.

Figure 6:
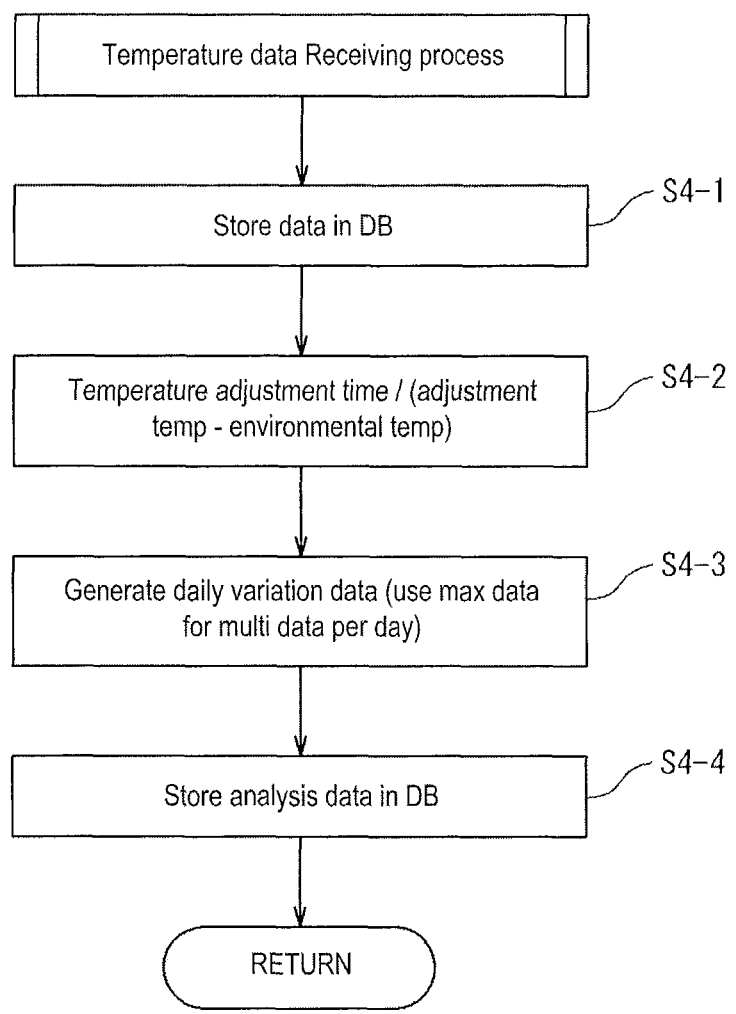
FIG. 6 is a flow chart showing the temperature data receiving process.

In the temperature adjustment data receiving process (step S4) shown in FIG. 6, when the receiving section 41 receives the raw data of the temperature adjustment data (temperature adjustment time) of the deterioration data and the identification of the clinical testing apparatus 2 that sent the data, the raw data are stored in the temperature adjustment data database 42c (step S4-1).

FIG. 7 shows the data table structure in the temperature adjustment database 42c. The temperature adjustment data (temperature adjustment time) forwarded from a plurality of clinical testing apparatuses 2 being managed by the management apparatus 4 are stored in the temperature adjustment database 42c. Note that the data forwarded from the plurality of clinical testing apparatuses are sequentially added to the storage of the temperature adjustment database 42c.

The data table structure shown in FIG. 7 includes the reception number, date received, time received, device code, apparatus ID similar to FIG. 4.

In FIG. 7, the items of environmental temperature and temperature adjustment time are added. The environmental temperature and temperature adjustment time are transmitted from the clinical testing apparatus 2.

When the temperature adjustment data are stored in the temperature adjustment database 42c (step S4-1), the analysis section 43 determines the time required to raise the object being heated by 1 degree based on the temperature adjustment time and the environmental temperature (step S4-2). This time is obtained by dividing the temperature adjustment time by the [temperature adjustment time (41° C.) minus the environmental temperature].

The analysis section 43 then generates the day-to-day variable data as analysis data based on the time determined in step S4-2 (step S4-2).

The generated analysis data are then stored in the temperature adjustment database 42d (step S4-3).

FIG. 8(a) shows the data table structure of the analysis data (day-to-day variation data) related to the temperature adjustment data by a specific clinical testing apparatus (apparatus ID: 567891). Note that the analysis data are generated for each of the plurality of clinical testing apparatuses by the analysis section 43. That is, the analysis data of each clinical testing apparatus 2 are stored in the temperature adjustment analysis database 42d.

In the data table structure of FIG. 8(a), the item on the horizontal axis is the day (day received). Among items on the vertical axis, "1st" and "2nd" are fields that store the [temperature adjustment data and environmental temperature] received first and the [temperature adjustment data and environmental temperature] received second on that day.

The "time" in the "1st" and "2nd" fields are the temperature adjustment raw data and "temp" is the environmental temperature.

"Avr." appearing on the vertical axis is where the average value (intra day average) of one or a plurality of temperature adjustment data of a given day are stored.

The raw data of temperature data and environmental temperature received by the receiving section is recorded in the temperature adjustment database 42c (step S4-1) or either the "1st" or "2nd" fields of the temperature adjustment analysis database of the clinical testing apparatus specified by the identification (apparatus ID) associated with the raw data in the pressure analysis database 42d.

Note that the initial raw data of the day are recorded in the "1st" field, and the second raw data are recorded in the "2nd" field.

The analysis section 43 calculates the average value of the day (weighted average) based on the time determined in step S4-2 as the day-today variation data generating process (step S4-3). The average value generated in step S4-3 is recorded in the "Avr." field of the temperature adjustment analysis database 42d of the clinical testing apparatus specified by the identification (apparatus ID).

When the WWW server 44 of the management apparatus 4 receives a display request (step S5) for the unit status information of a specific clinical testing apparatus from a terminal device connected via the network, the graph shown in FIGS. 5(a), (b), and (c) or FIGS. 8(a) and (b) is displayed on the terminal device as a display process (step S6). Note that the display also may be the display device of the management apparatus 4.

The display request received by the management apparatus 4 includes the identification (apparatus ID) of the clinical testing apparatus for which the unit status information is wanted via display. The display request also includes information indicating the type (air pressure source unit, heating unit) of unit.

When the display request is received, if the type of unit specified in the display request is an air pressure source unit, the display processor 44 of the management apparatus 4 searches the pressure analysis database 42b based on the identification contained in the display request, and the day-to-day average data Avr. and the moving average data M. Avr. are extracted for the clinical testing apparatus specified by the identification. If the type of unit specified in the display request is a heating unit, the display processor 44 searches the temperature adjustment analysis database 42d based on the identification contained in the display request, and extracts the day-to-day average data Avr. for the clinical testing apparatus specified by the identification.

The display processor 44 generates graphs by plotting the extracted data along a time series, and transmits the generated data to the terminal device that forwarded the display request.

FIG. 5(a), (b), (c) shows the unit status information of the air pressure source unit 2b identified (device ID) as 470842 as graphs in time-series format. FIG. 5(b) shows the graphs of the day-to-day variable data stored in the "Avr." field of the air pressure analysis database 42b as graphs on the vertical axis, and FIG. 5(c) shows the moving average data stored in the "M. Avr." field of the database 42b as graphs on the vertical axis.

FIG. 8(b) shows the unit status information of the heating unit 2c identified (device ID) as 567891 as graphs in time-series format. FIG. 8(b) shows the day-to-day variably data stored in the "Avr." field of the temperature adjustment analysis database 42d as graphs on the vertical axis.

In the graphs in FIGS. 5(b), (c), and FIG. 8(b), the days for which there are no analysis data in the analysis databases 42b and 42d are omitted from the time series.

In the graphs of FIGS. 5(b), (c), and FIG. 8(b), analysis data of each day that exceed a predetermined threshold value are highlighted with an X mark. In the example of FIG. 5(c), the threshold value is set at 9,000 (msec), and plots that exceed 9,000 msec are highlighted. In the example of FIG. 8(b), the threshold value is set at 30 sec, and plots that exceed 30 sec are highlighted. Note that the check for exceeding the threshold (step S8) is described later.

As shown in FIGS. 5(a), (b), and (c) of the present embodiment, the manager operating the management apparatus and the service person performing maintenance and inspection of the clinical testing apparatus can visually comprehend the recent trend of deterioration of the air pressure source unit 2b since the past unit status information (time required to reach standard pressure) of the air pressure source unit 2b is shown in time-series format. As shown in FIGS. 8(a) and (b), the manager or service person can visually comprehend the recent trend of deterioration of the heating unit 2c since the past unit status information (heating efficiency) of the heating unit 2c is displayed in time-series format. The manager or service person visually comprehends the deterioration trend via the gradually increasing values, and, hence, comprehends the deterioration condition before failure of the unit. Therefore, the manager or service person can infer whether the deterioration can be eliminated by adjusting and repairing part of the unit or the deterioration will continue unless the unit is replaced based on the deterioration trend. The manager or service person may plan a visit to the facility at which the clinical testing apparatus 2 is installed for inspection or part replacement to eliminate the deterioration of the unit. Hence, apparatus down time can be reduced by preventing failure of the clinical testing device 2 before the fact.

Although the raw data (parameters) stored in the databases 42a and 42c may be shown in the display process, noise fluctuation may be eliminated to show the parameter variation over a comparatively long time by displaying the analysis data (average, moving average) generated based on the raw data (parameters).

The day-to-day variable data (first information) is suited to comprehend unexpected abnormalities each day, and the moving average data (second information) is suited to comprehend the trend of data variation over a comparatively long time. In the display process, the manager or service person easily comprehends the unit status information of a unit by displaying the result of processing (statistical processing) the raw data (parameters) by a plurality of different method.

Figure 9:
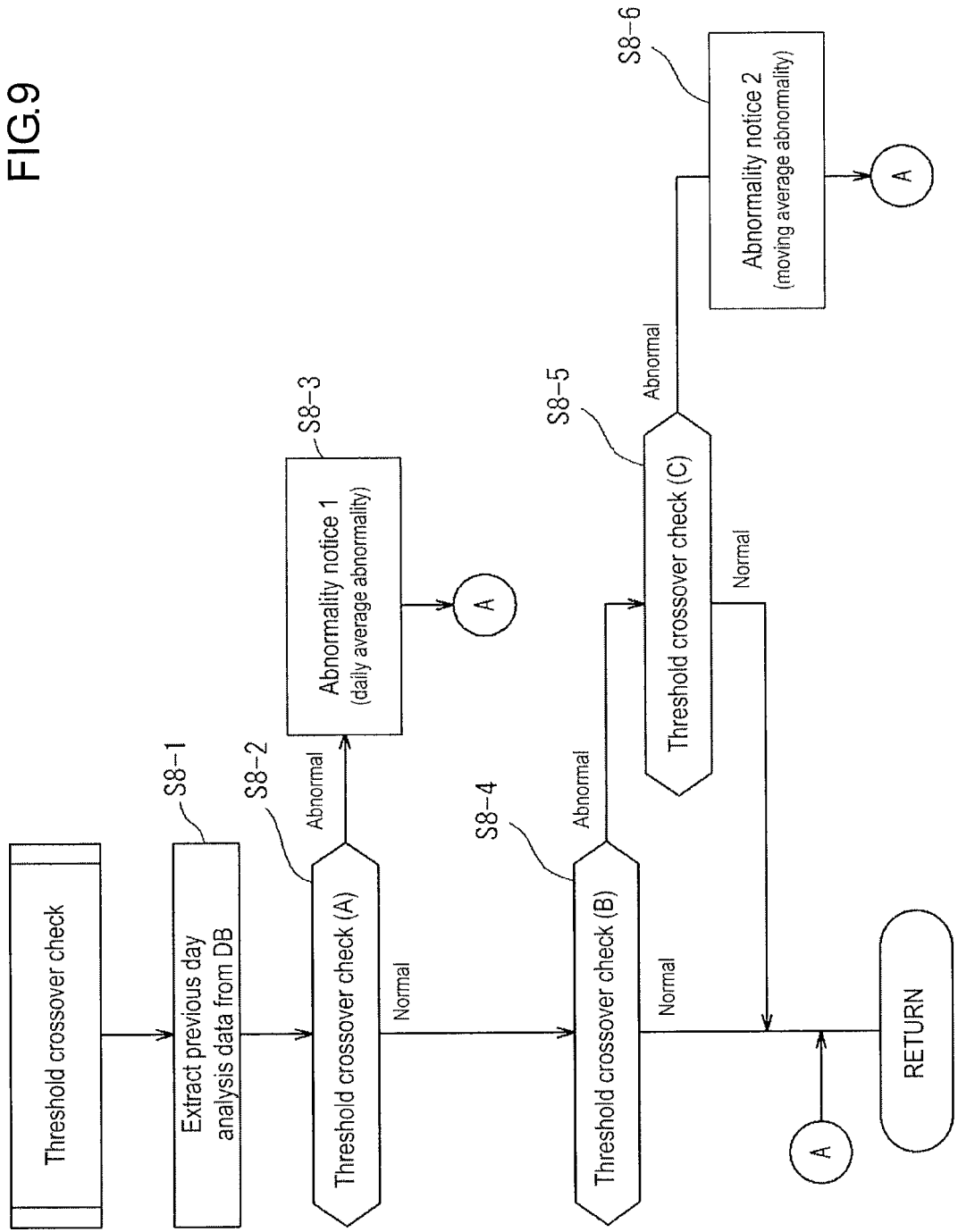
FIG. 9 is a flow chart showing the crossed threshold checking process.

The analysis section 43 of the management apparatus 4 performs the process shown in FIG. 9 as the threshold crossover check (step S8) at a predetermined time (for example, 6:00 AM). In the threshold crossover check, the analysis data of the previous day are extracted from the analysis databases 42b and 42d (step S8-1).

The analysis section 43 checks whether the day-to-day variation data among the analysis data exceed a predetermined threshold A (step S8-2). When the day-to-day variation data exceed the threshold A, a notice is issued indicating that an abnormality occurred in the day-to-day average (step S8-3).

Then, the analysis section 43 checks whether the moving average data of the previous day exceeds a predetermined threshold B (step S8-4). When the moving average data exceed the threshold B, a determination is made as to whether the moving average data that exceed the threshold B do so for five consecutive days (step S8-5). When the moving average data that exceed the threshold B are determined to do so for five consecutive days in step S8-5, a notice is issued indicating an abnormality occurred in the moving average (step S8-4).

The notices issued in steps S8-3 and S8-6 are issued by transmitting E-mail from the management apparatus 4 to the client management system 5. The E-mail includes the name of the facility where the clinical testing apparatus is installed, the name of the person responsible for servicing the clinical testing apparatus, apparatus ID, model name, name of the unit in which the abnormality was detected, type of abnormality (day-today average abnormality or moving average abnormality).

Figure 10:
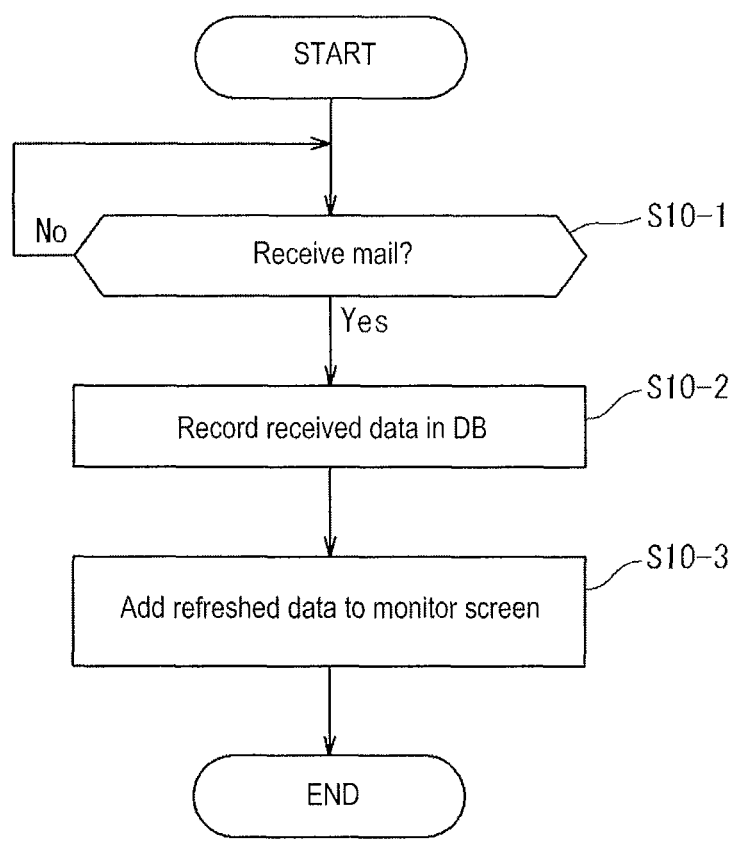
FIG. 10 is a flow chart showing the data receiving process in a customer management system.

When the client management system 5 receives the E-mail from the management apparatus 4 as shown in FIG. 10 (step S10-1), the received data are recorded in the database of the client management system 5 (step S10-2). The new data acquired by E-mail are also displayed on a monitor screen of the client management system 5 (step S10-3). Hence, the person in charge of the client management system 5 can contact the person in charge of servicing the clinical testing apparatus with the detected abnormality. The contacted person in charge of service can access the maintenance management apparatus 4 (WWW server 44), to survey the data of FIGS. 5(b), (c), or FIG. 8(b), to visit the facility for repair operations as needed.

Note that the service person can access the maintenance management apparatus 4 whenever required even without an abnormality notice.

The present invention is not limited to the above embodiment and may be variously modified.

Although a blood analyzer is used as an example of a clinical testing apparatus in the above embodiment, the present invention is not limited to this example. For example, the clinical testing apparatus also may be a blood coagulation time measuring apparatus for analyzing plasma or serum as a clinical sample, an immunoanalyzer, biochemical analyzer, or urine analyzer for analyzing urine as a clinical sample.

Although the example of the above embodiment described the time required to reach a standard pressure as a parameter that changes according to the deterioration of a particular compressor 21 of the air pressure source unit 2b, the present invention is not limited to this example. For example, the amplitude of fluctuation (pressure fluctuation amplitude) of the output of the regulator 22 while measurement is performed by the measuring unit 2a also may be used as the deterioration parameter of the air pressure source unit 2b.

When the regulator 22 of the air pressure source unit 2b deteriorates, the pressure fluctuation amplitude increases during the measurement operation. This deterioration occurs before complete failure of the regulator 22 occurs and gradually increases over time, hence gradually increasing the pressure fluctuation amplitude. The deterioration condition of the air pressure source unit 2b also can be monitored using the pressure fluctuation amplitude.

The pressure value from the pressure sensor 23 is usually input to the processor 28 of the clinical testing apparatus 2. The processor 28 starts monitoring the pressure value after the air pressure source unit 2b is started and the output of the regulator 22 reaches the standard pressure. Specifically, the processor 28 stores the difference between the standard pressure and the maximum or minimum pressure value as the pressure fluctuation amplitude based on the standard pressure among the pressure values received from the pressure sensor 23 after the standard pressure has been reached. When the clinical testing apparatus 2 is shut down, the processor 28 transmits the stored pressure fluctuation amplitude from the transmitting section 29 to the management apparatus 4. Thereafter, the data processing performed by the management apparatus 4 is identical to the data processing of the time required to reach standard pressure of the above embodiment.

According to the above configuration, it is possible to monitor not only the trend of abnormality of the compressor 21, but also the trend of abnormality of the regulator 22.

The embodiment using the pressure fluctuation amplitude as pressure data may also be configured to also use the time required to reach standard pressure. In this case, a more multi-faceted monitoring is possible for abnormality of the air pressure source unit 2b by jointly using two parameters.

In addition to using the change according to deterioration of a unit as a parameter, the disposal time from the waste chamber, intensity of the laser diode emission of the measuring unit, and frequency of abnormality detection notice in measurement data also may be used. The waste unit disposal tube may be gradually blocked so as to gradually lengthen the disposal time as the blockage develops. The intensity of the laser diode may decrease as the laser diode deteriorates. When the parts of the fluid system of the measuring unit become soiled, the measurement data may manifest abnormal value, hence increasing the frequency of the abnormal detection flag.

Although the above embodiment is described by way of example in which the present invention is applied to a system in which the clinical testing apparatus and the management apparatus are connected by a network, the present invention is not limited to this example inasmuch as the invention also may be applied to a standalone clinical testing apparatus. Specifically, the clinical testing apparatus 2 may have a structure equivalent to the database 42 of the management apparatus 4, wherein the unit status information can be sequentially displayed when a user issues a display request to the clinical testing apparatus 2 and the clinical testing apparatus 2 searches the database 42.

Although the clinical testing apparatus 2 transmits to the management apparatus 4 each time a deterioration parameter is acquired in the above embodiment, the present invention is not limited to this transmission timing. For example, the clinical testing apparatus 2 may store the deterioration parameters and transmit the stored deterioration parameters in a batch to the management apparatus 4 at a predetermined time. Alternatively, when the management apparatus 4 receives a display request, the management apparatus 4 may transmit a data request to the clinical testing apparatus 2, and the clinical testing apparatus 2 then transmits the deterioration parameters according to the data request.

What is claimed is:

1. A method for managing a clinical testing apparatus having a plurality of units and that performs a test on a clinical sample by use of the units, wherein one of the units comprises a pneumatic power source for moving a liquid containing a clinical sample, the method comprising:
   acquiring, from the clinical testing apparatus, predictive pressure and time data of the pneumatic power source at a plurality of points in time after the pneumatic power source is started until the pressure reaches a predetermined level indicating normal operation;
   storing parameters or analysis results that are obtained by analyzing the predictive pressure data,
   wherein at least one parameter comprises a time from when the pneumatic power source is started until the pneumatic power source reaches the predetermined level; and
   displaying a graph of the predictive pressure data in a sequential time-series format and values of the stored parameters of the stored analysis results to determine a degree of deterioration of the pneumatic power source.

2. The method of claim 1, further comprising acquiring the analysis results by statistically analyzing the pressure data acquired at a plurality of points in time within a predetermined period.

3. The method of claim 2, wherein the statistical analysis includes:
   a first statistical process of acquiring a first analysis result by statistically analyzing the pressure data acquired within a predetermined first period; and
   a second statistical process of acquiring a second analysis result by statistically processing the pressure data within a second period that is longer than the first period or comprises a plurality of first analysis result,
   wherein the displaying includes one or both of simultaneously or selectively displaying the first and second analysis results.

4. The method of claim 3, wherein the statistical analysis further includes an excluding process of excluding parameters that fall below a lower limit threshold of an object of the statistical analysis.

5. The method of claim 3, wherein the first statistical process includes acquiring an average value of the pressure data acquired during one day, and the second statistical process comprises acquiring a moving average value of the average values of the pressure data over several consecutive days.

6. The method of claim 3, further comprising determining whether the first analysis result exceeds a threshold value, and notifying a user by executing an alert when the first analysis information exceeds the threshold value.

7. The method of claim 3, further comprising determining whether the second analysis results consecutively exceed a threshold value, and notifying a user by executing an alert when the consecutive second analysis results exceed the threshold value.

8. The method of claim 1, wherein at least one parameter comprises a time from when the pneumatic power source starts to make an air pressure until the air pressure reaches the predetermined level.

9. The method of claim 1, wherein the clinical testing apparatus further comprises a heater, and the method further comprises acquiring, from the clinical testing apparatus, temperature data including a time required for the heater to raise a temperature of an object to a predetermined temperature.

10. A clinical testing system comprising:
    a maintenance computer having a memory and a display; and a clinical testing apparatus having a pneumatic power source for moving a liquid containing a clinical sample and connected to the maintenance computer via a network, the clinical testing apparatus further comprising:
a measuring unit configured to test a clinical sample; and
a transmitting section for transmitting to the maintenance computer parameters comprising time, pressure, and temperature data after the pneumatic power source is started until the pressure reaches a predetermined level indicating normal operation;
wherein the transmitting section transmits the parameters with a predetermined transmission timing;
the memory associates and stores the parameters transmitted from the transmitting section or an analysis result acquired by analyzing the parameters with an identification of the clinical testing apparatus that transmitted the parameters,
wherein at least one parameter comprises a time from when the pneumatic power source is started until the a pneumatic power source reaches the predetermined level; and
the display shows, in response to a display request from a terminal device, a graph of at least one of the stored parameters or the analysis result of the identified clinical testing apparatus in a time-series format to determine a degree of deterioration of the pneumatic power source.

11. A management system connected via a network with a clinical testing apparatus having a pneumatic power source for moving a liquid containing a clinical sample that performs a test on the clinical sample by use of the pneumatic power source, the management system comprising:
a receiving section for receiving a parameter comprising predictive pressure and time data after the pneumatic power source is started until the pressure reaches a predetermined level indicating normal operation, the parameter transmitted from the clinical testing apparatus at a predetermined timing, the parameter being variable according to deterioration of the pneumatic power source;
a data storage for storing the received parameter or analysis results that are obtained by analyzing the parameter, in association with an identification of the clinical testing apparatus that transmitted the parameter; and
a data provider for providing data on a screen, the data comprising a graph of the parameter or the analysis results of the identified clinical testing apparatus is shown in a time-series format.

12. The system of claim 11, further comprising analyzing section for acquiring the analysis results by statistically analyzing the parameter acquired at a plurality of points of time within a predetermined period.

13. The system of claim 12, wherein the analyzing section acquires a first analysis result by statistically processing a plurality of parameters acquired within a predetermined first period;
acquires a second analysis result by statistically processing a plurality of parameters acquired within a second period that is longer than the first period and/or a plurality of first analysis results; and
the data provider provides screen data for showing the first and second analysis results simultaneously or selectively.

14. The system of claim 12, wherein the analyzing section excludes predictive pressure data that falls below a lower limit threshold of an object of the statistical analysis.

15. The system of claim 13, wherein the analyzing section acquires the average value of the pressure data acquired during one day as the first analysis result; and acquires a moving average value of the average values over several consecutive days as the second analysis result.

16. The system of claim 13, wherein the analyzing section determines whether the first analysis result exceeds a threshold value, and transmits a notice to a terminal device connected via a network when the first analysis result exceeds the threshold.

17. The system of claim 13, wherein the analyzing section determines whether the consecutive second analysis results exceed a threshold value, and transmits a notice to the terminal device connected to the management system via a network when the second analysis results exceed the threshold value.

* * * * *